United States Patent [19]

Lanza et al.

[11] Patent Number: 5,090,040
[45] Date of Patent: Feb. 18, 1992

[54] DATA ACQUISITION SYSTEM FOR RADIOGRAPHIC IMAGING

[75] Inventors: Richard C. Lanza, Brookline; Joseph R. Votano, Tewksbury; Tomas Russ, Brookline, all of Mass.

[73] Assignee: Expert Image Systems, Inc., Somerville, Mass.

[21] Appl. No.: 321,996

[22] Filed: Mar. 10, 1989

[51] Int. Cl.[5] .................. G01N 23/04; H05G 1/64; G06F 15/00

[52] U.S. Cl. ........................ 378/62; 378/8; 378/53; 378/54; 378/162; 378/99; 378/901; 364/413.13; 364/413.15

[58] Field of Search .............. 378/53, 8, 54, 62, 99, 378/901; 250/336.1, 389, 385, 374; 364/413.13, 413.15

[56] References Cited

U.S. PATENT DOCUMENTS

| | | | |
|---|---|---|---|
| 3,639,764 | 2/1972 | Olson et al. | 250/83.3 D |
| 3,715,588 | 2/1973 | Rose | 250/71.5 S |
| 3,944,830 | 3/1976 | Dissing | 250/358 R |
| 4,494,141 | 1/1985 | Altekruse | 364/413.15 |
| 4,504,909 | 3/1985 | Acharya et al. | 364/413.15 |
| 4,722,097 | 1/1988 | Haendle | 378/99 |
| 4,802,093 | 1/1989 | Ema | 378/99 |
| 4,803,711 | 2/1989 | Tsujii et al. | 378/901 |
| 4,830,012 | 5/1989 | Riederer | 364/413.13 |
| 4,887,211 | 12/1989 | Thiel et al. | 378/901 |
| 4,949,175 | 8/1990 | Wind | 364/413.13 |
| 4,956,859 | 9/1990 | Lanza et al. | 378/99 |

FOREIGN PATENT DOCUMENTS 180482 7/1986 European Pat. Off. .
WO86/07531 12/1986 PCT Int'l Appl. .

Primary Examiner—Edward P. Westin
Assistant Examiner—Kim-Kwok Chu
Attorney, Agent, or Firm—Thomas J. Engellenner

[57] ABSTRACT

A data acquisition system is disclosed for use in radiographic imaging. The acquisition system includes at least two memory banks for storing radiographic data from a radiation detector, acquisition circuitry for sensing radiographic data when transmitted by the detector and for writing such data into one of the memory banks, and a controller for selecting a memory bank for storage of the data, and for switching from one memory bank to another, as well as for reading data from one or the other memory banks when such memory bank is not actively acquiring data.

8 Claims, 11 Drawing Sheets

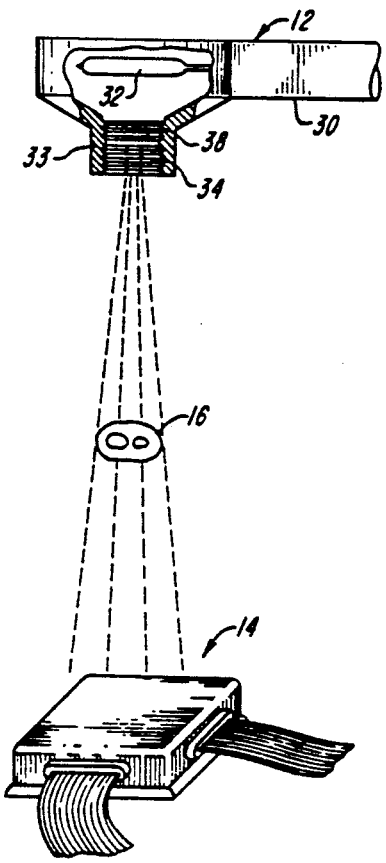
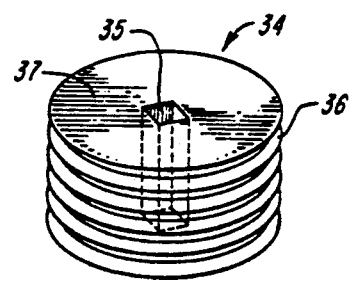
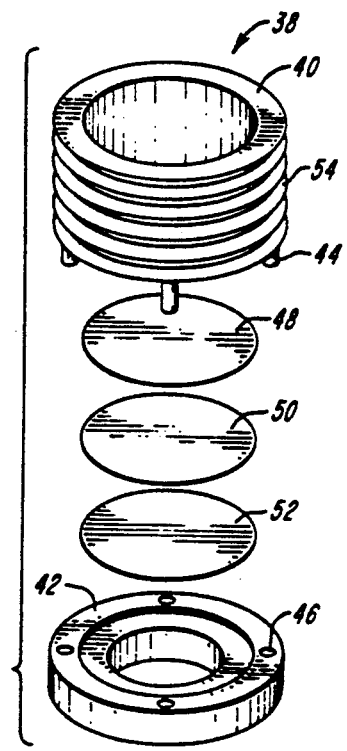
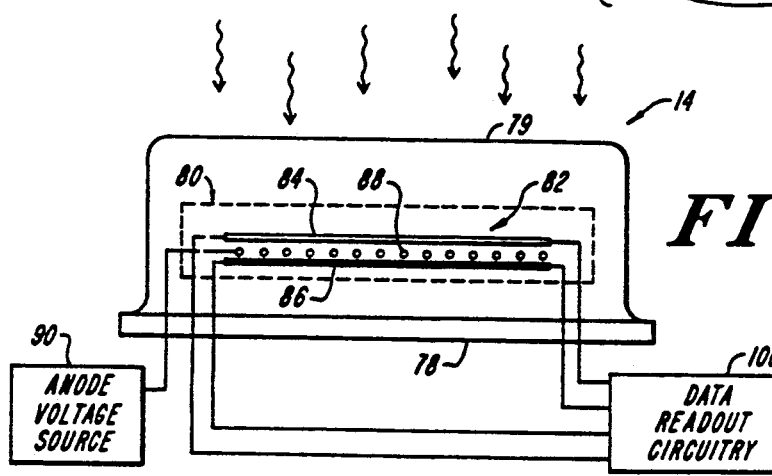
FIG. 3
FIG. 4
FIG. 5
FIG. 6

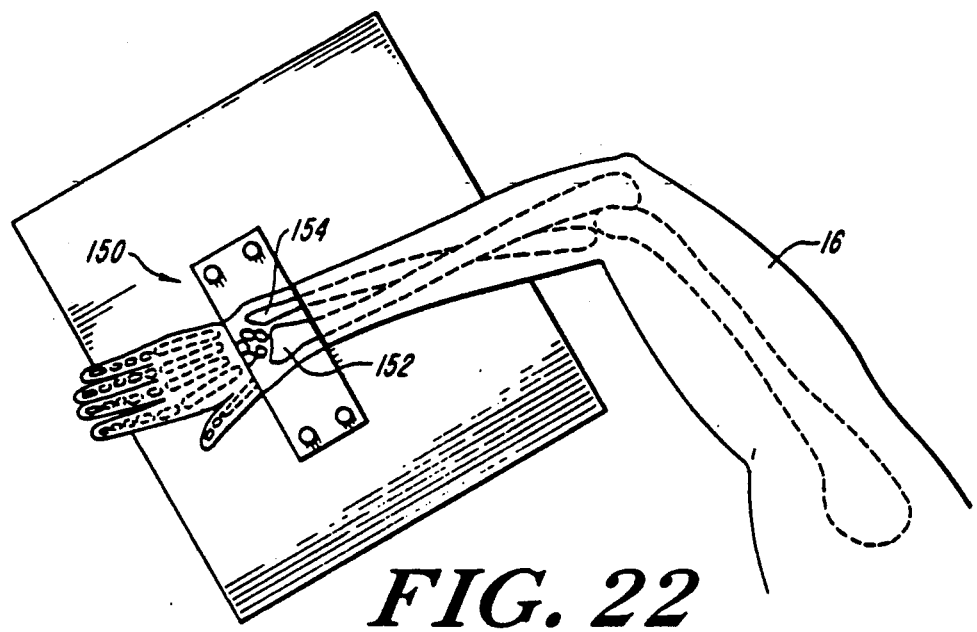
FIG. 22
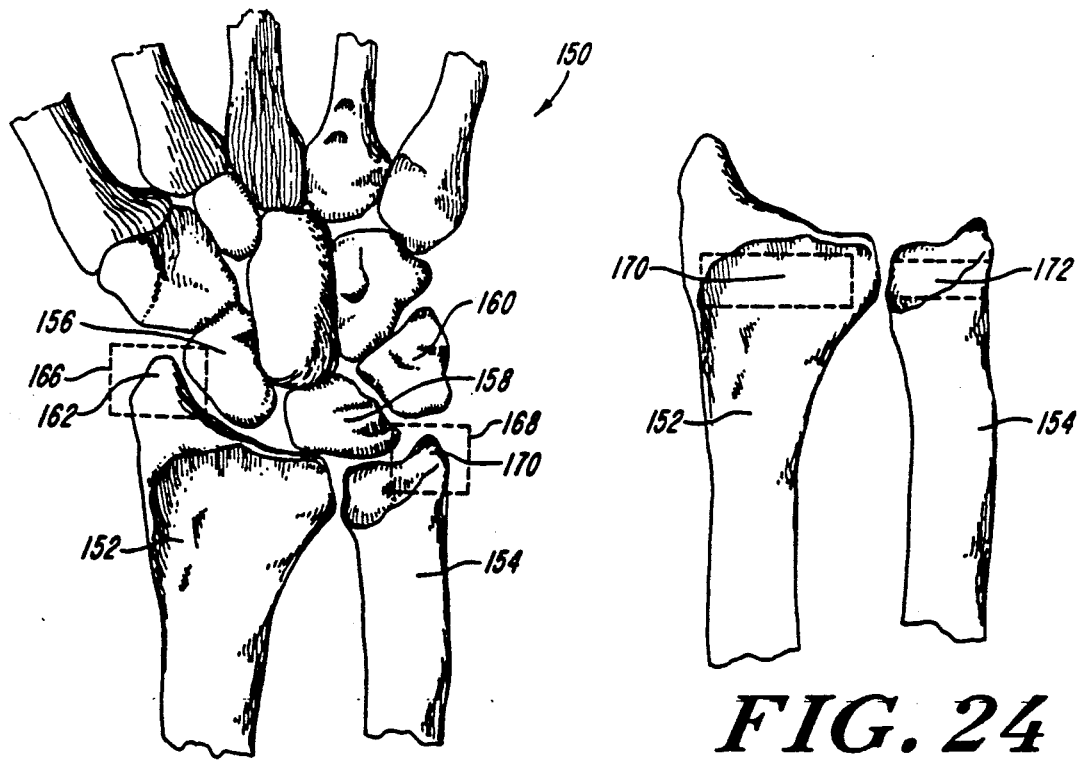
FIG. 23
FIG. 24

DATA ACQUISITION SYSTEM FOR RADIOGRAPHIC IMAGING

BACKGROUND OF THE INVENTION

The technical field of this invention is radiology and, in particular, bone absorptiometry by radiographic measurements.

The depletion of bone mineral content, typically referred to as osteoporosis, is a common consequence of a variety of diseases and natural aging processes. In addition to metabolic bone diseases and aging, bone minerals can be lost as the result of drugs, stress, dietary deficiencies, pregnancy or lactation. When skeletal bone mass drops below the level necessary to provide mechanical support, the depletion of bone mineral content becomes an important cause of morbidity, particularly in elderly patients.

Unfortunately, at present there are no reliable and inexpensive systems for gauging bone mineral content (BMC) with any high degree of precision, particularly during the early stages of osteoporosis or other mineral depletion disorders when dietary supplements and therapeutic agents may reverse the course of demineralization and prevent debilitating fractures or otherwise slow the progress of the disease.

Conventional methods for determining bone mineral content typically involve measurements of radiation absorption in the bone. U.S. Pat. No. 3,715,588 issued to Rose on Feb. 6, 1973, is illustrative of a prior art "bone scanner" in which a collimated X-ray beam is passed through a bone (e.g., the wrist) and detected by a radiation detector mechanically coupled to the X-ray source. The system scans back and forth across the bone to produce a complete measurement of the bone and surrounding tissue. Because of inherent differences in tissue and bone absorption, bone density (and, hence, mineral content) can be inferred from a logarithmic ratio of the intensity of radiation detected after transmission through the two media.

Other techniques for determining bone mineral content using stationary "area" scintillation cameras have also been proposed. See, for example, DePuey et al., "Bone Mineral Content Determined by Functional Imaging", Vol. 16, *J. Nuclear Medicine*, pp 891–895 (1975), for a discussion of such scintillation camera-based systems. The area detectors similarly rely upon the inherent differences between tissue and bone absorption of radiation to compute bone density values.

Both linear scanning and area detection systems suffer from a lack of precision in measurement. In scanning systems, the motion of the radiation source and detector can result in image blurring, particularly if patient motion occurs. In area systems, the resolution of the detector (e.g., a scintillation medium) can be a limiting factor.

These limitations typically are compounded by data acquisition problems when images are formed on an event-by-event basis; that is, when individual radiation photons are detected and the position of impact on the detector is digitized for each radiation event. Data can be transferred from the detector on either a "frame" (histogramming) basis by addressing and incrementing specific memory locations corresponding to spatial locations, or on a "list" basis by writing a series of digital values corresponding to locations into sequential memory locations.

Data acquisition rates are often limited by the inability of imaging systems to transfer data continuously, in either frame or list mode. There exists a need for a continuous data acquisition system, as well as systems which can transfer data, without interrupting acquisition activity, to processing, display and/or storage modules to permit real-time radiographic imaging and bone density or mineral content measurements.

SUMMARY OF THE INVENTION

A data acquisition system is disclosed for use in radiographic imaging. The acquisition system includes at least two memory banks for storing radiographic data from a radiation detector, acquisition circuitry for sensing radiographic data when transmitted by the detector and for writing such data into one of the memory banks, and a controller for selecting a memory bank for storage of the data, and for switching from one memory bank to another, as well as for reading data from one or the other memory banks when such memory bank is not actively acquiring data.

The data acquisition system of the present invention is particularly useful in acquiring radiographic data from a spatial or area radiation detector, such as a multi-wire proportional chamber (MWPC), a scintillation screen device, or a photostimulatable luminescence measuring device. Alternatively, the data acquisition system can be employed with scanning radiation detectors. The memory banks can be organized such that the elements of the memory bank correspond to spatial locations in an area detector or colinear locations within a scanning detector.

The memory banks of the data acquisition system can be organized to store data on a frame or histogramming basis in order to generate radiographic intensity images and, in one embodiment, this system further includes incrementing unit for incrementing individual elements of the memory means in response to individual radiation events detected by the radiation detector. Alternatively, the memory banks and the acquisition circuitry can cooperate to receive and store data transmitted by the detector on a list basis.

The controller in the data acquisition system of the present invention can further include apparatus for determining when one of the memory banks has reached a predetermined capacity level, and for switching from one memory bank to another when the level has been reached. The acquisition system can also include means for storing calibration data in conjunction with the radiographic data. In one illustrated embodiment, the radiation absorption profiles of two dissimilar calibration materials (e.g., a tissue equivalence material and a bone equivalence material) are stored in the memory bank along with the radiographic image data. Calibration of the radiographic imaging can be achieved by comparing the intensity of radiation transmitted through the two equivalence materials. A ratio of these values (preferably in logarithmic form) can then be compared with a predetermined measurement standard, thus permitting an operator to dynamically adjust the system until a desired measurement constant is achieved.

The data acquisition system of the present invention can further include a computer interface, connected to the controller and the memory banks for reading data from the memory banks to an auxilliary device, such as a data processing module, a data display module, or a data storage module.

The invention will next be described in connection with certain illustrated embodiments. However, it should be clear that various changes, additions and subtractions can be made without departing from the spirit or the scope of the invention.

BRIEF DESCRIPTION OF THE DRAWINGS

FIG. 3 is a more detailed schematic diagram of the radiation source and detection of the system of FIG. 2;

FIG. 4 is a more detailed schematic illustration of the beam collimator of FIG. 3;

FIG. 5 is an exploded schematic illustration of the beam filter of FIG. 3;

FIG. 6 is a schematic side view of a multi-wire detector module useful in the system of FIG. 2;

FIG. 22 is a schematic illustration of a patient X-ray image (showing non-imaged bones in phantom) in accordance with the present invention;

FIG. 23 is a more detailed view of an X-ray image illustrating a method of identifying bone reference points according to the present invention;

FIG. 24 is another detailed view of an X-ray image illustrating a method of defining bone analysis regions according to the present invention.

DETAILED DESCRIPTION

Figure 1:
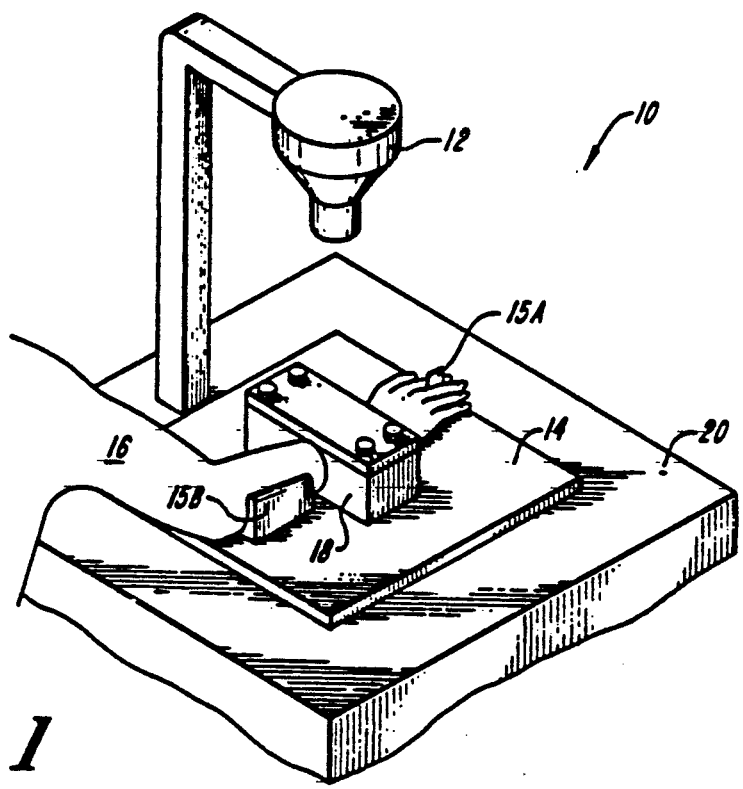
FIG. 1 is an isometric view of a radiographic imaging system according to the present invention.

FIG. 1 is an isometric view of a radiographic imaging system 10 for analyzing biological structures according to the present invention consisting of a radiation source 12, which transmits a beam of radiation to detector module 14. Disposed between the radiation source 12 and the detector module 14 is the limb of a patient 16, which is secured in place by a limb positioning apparatus 18 and registration means 15A, 15B which prevents the limb from pivoting about the positioning apparatus 18 in operation. The detector module 14 and the limb positioning apparatus 18 and the registration means 15A, 15B conveniently can be incorporated into a housing 20 so that the patient can sit while the procedure is being conducted.

Figure 2:
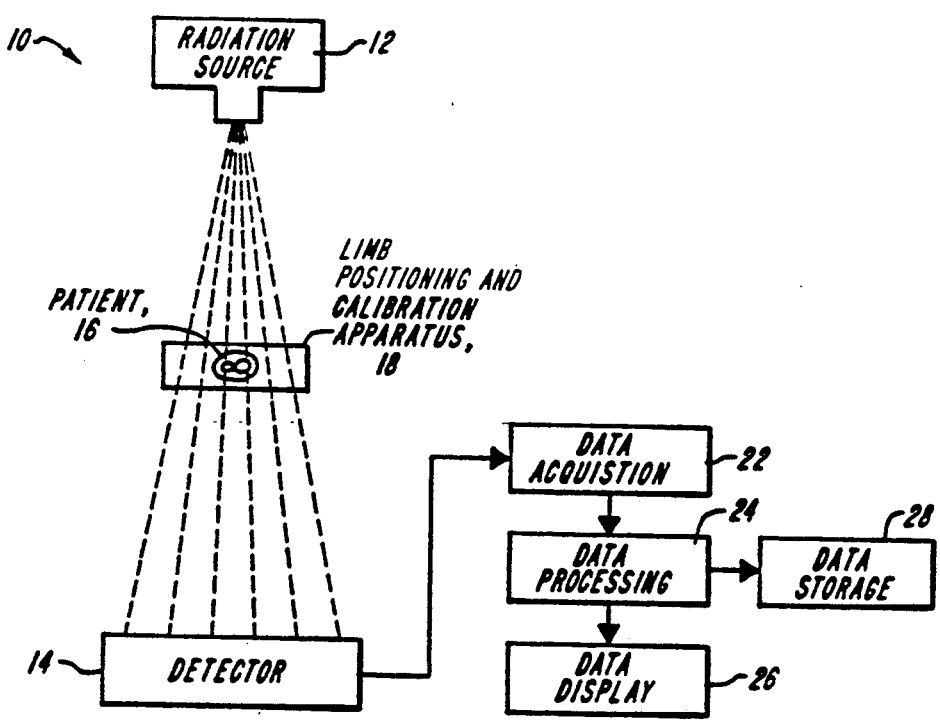
FIG. 2 is a schematic block diagram of a radiographic imaging system according to the invention.

FIG. 2 is a more detailed schematic block diagram of the radiographic imaging system as shown, including radiation source 12, detector module 14, limb positioning and calibration apparatus 18, data acquisition module 22, data processing module 24, data display module 26 and data storage module 28. Radiation emitted by the radiation source 12 passes through the patient's limb (e.g., the wrist) 16 and is detected by detector module 14 and converted therein to digital data. The data is then transferred to the acquisition module 22 where a radiographic image of the patient's limb is built up over time. The images formed in the acquisition module can be analyzed in the data processing module 24 (e.g., to detect osteoporosis or other changes in bone mineral content), displayed by the display module 26 and/or stored for subsequent analysis or display in data storage module 28.

FIGS. 3-7 are more detailed schematic illustrations of the radiation source 12 and detector module 14. As shown in FIG. 3, radiation source 12 includes a radiation head assembly 30 which houses a radiation emitter 32, such as a radioisotope or, preferably, an X-ray tube operable to generate photon radiation having maximum energy levels, for example, on the order of about 45 to about 70 KeV and, preferably, about 55 KeV. Such X-ray tubes are available commercially from a variety of sources. One such commercially available tube is the Model OIX-15 dental X-ray tube (Eureka Company, Chicago, Ill.).

Also shown in FIG. 3 is a detector module 14 which preferably is an area detector capable of determining the spatial intensity of radiation emitted by the radiation source 12 and transmitted through the patient's limb 16. One such area detector is a multi-wire, proportional chamber detector, described in more detail below in connection with FIGS. 6 and 7. Other area detectors which can be employed in the present invention include scintillation screen devices, employing gadolinium sulfate or lanthanum sulfate crystals and associated electronic imaging (i.e., CCD) elements, or photosimulatable luminescence (PSL) measuring devices. Detectors of these types are commercially available, for example, from Kodak (Rochester, N.Y.) or Fuji (Tokyo, Japan).

The radiation head assembly 30 shown in FIG. 3 also includes a threaded barrel 33 into which can be inserted a collimator assembly 34 and a filter assembly 38. In FIG. 4, a more detailed schematic illustration of a collimator assembly 34 is shown consisting of a machined metal (i.e., lead) body 37 having a central hole 35 and peripheral threads 36 so that it can be screwed into the threaded barrel 33 of the radiation head assembly.

FIG. 5 is an exploded schematic illustration of the beam filter assembly 38, including a filter housing 40 and cover plate 42 which can be connected by bolts 44 on the housing through holes 46 on the cover plate via nuts or other suitable attachment means. Disposed within the filter assembly is one or more filter elements. In the illustration, three such filter elements 48, 50 and 52 are shown. In one preferred embodiment of the invention, three filter elements of gadolinium, silver and tin, each having a thickness on the order of about 0.08 millimeters can be employed.

More generally, in the invention, it is preferable to employ at least one filter element which operates to reduce the transmission of high energy photons in conjunction with a detector module having a characteristic response which is relatively insensitive to low energy photons, such that the source filter and the detector module cooperate to measure the intensity of photons within a narrowed band of energy levels.

The principal of operation is that the detector is chosen such that it has an energy response which increases efficiency rapidly above a defined energy level, known as the "K-edge", for a particular detector material. Xenon gas-based detectors have a K-edge at about 35 KeV. Barium-based PSL imaging plates have a similar K-edge at about 37 KeV. Gadolinium scintillation screens have a K-edge at about 50 KeV. The filter is chosen, such that its K-edge is higher than that of the detection, such that the resultant system acts as a bandpass filter with a lower limit defined by the K-edge of the detector and an upper limit defined by the K-edge of the filter.

In one preferred embodiment, at least one filter element has an elemental composition consisting of one or more of the lanthanide metals, such as lanthanum, cerium, praseodymium, neodymium, promethium, samarium, europium, gadolinium, terbium, dysprosium, holmium, erbium, thulium, ytterbium, lutetium or alloys thereof. This filter element can be employed alone or in combination with one or additional filter elements having an elemental composition of silver, cadmium, indium, tin or alloys thereof. As noted above, one particularly useful combination of filter elements is the ternary combination of gadolinium, silver and tin. Each filter element can have a thickness ranging from about 0.01 to about 1.0 millimeters, preferably ranging from about 0.05 to about 0.5 millimeters.

The collimator 34 is employed to eliminate scattering effects that may be caused during the filtering processes and produces a beam of radiation of appropriate size and shape for passage through the patient limb undergoing radiographic imaging to the detector module.

In FIG. 6, a multiwire proportional chamber (MWPC) device 80 is illustrated as part of detector module 14. The chamber 80 is filled with a gas 82, which typically comprises xenon (Xe) and one or more buffer or additive gases, and contains an X-cathode grid 84, a Y-cathode grid 86 and an anode grid 88. The MWPC device 80 can be incorporated into a housing 78 having a window or otherwise radiation-transparent upper surface 79. Voltage source 90 produces a positive charge on the anode grid 88. The cathode grids 84, 86 are connected to data readout circuitry 100 to sense ionization events which occur when the photon radiation ionizes the xenon gas molecules within the chamber 80 and when the electrons, resulting from such ionization, drift to the positive anodes where charge multiplication takes place.

Figure 7:
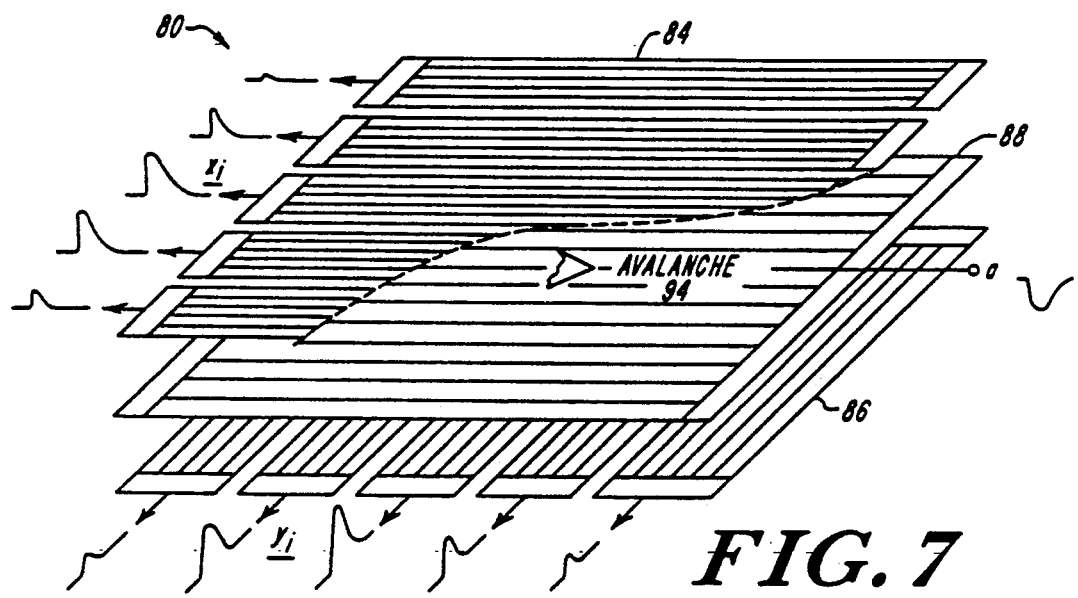
FIG. 7 is a more detailed schematic illustration of the cathode and anode grids of the detector of FIG. 6.

In FIG. 7, the operation of the MWPC device 80 is further illustrated schematically. In the simplified illustration, five X-cathode and five Y-cathode lines 84, 86 are disposed in orthogonal relationship (each of which is actually composed of a series of parallel wires which are ganged together) forming a 5×5 coordinate matrix. The X-grid 84 and the Y-grid 86 are separated from each other by an anode grid 88. When a photon of sufficient energy strikes a xenon gas molecule, the gas molecule is ionized, producing an electron-ion pair. The electron drifts towards the anode where the intense-field around the anode results in charge multiplication. The resulting avalanche 94 of electrons is sensed as a positive charge on the nearest wires of both the X-cathode and the Y-cathode grids, as well as a negative charge on the anode grid. The coincidence of the X-cathode signals, $X_i$, the Y-cathode signals, $Y_i$, and the anode signal, a, permits the detector to accurately pinpoint the location of the radiation-induced ionization event.

In practice, the grids are larger and finer than shown in FIG. 7 to provide higher spatial resolution. For example, one embodiment for wrist imaging can employ 160 parallel Y-cathode wires and 80 parallel X-cathode wires, which are ganged as pairs to provide a 40×80 location grid. The spacing between adjacent wires can be approximately 1 millimeter. Alternatively, the cathode grids can be constructed on radiation-transparent (e.g., polyimide) printed circuit boards, for example, having copper strips 4–5 millimeters wide separated from each other by gaps of about 0.1 to about 0.5 millimeters in width.

The anode grid 88 can be similarly constructed of a plurality of thin parallel (e.g., 20 micrometer gold plated tungsten) wires. The anode wires, however, can be all wired together and, in operation, are all at the same voltage determined by the voltage source 90. The voltage will depend upon the pressure of the Xe gas within the chamber, as well as the spacing between the anode wires, and the anode-to-cathode spacing. For a typical pressure of 3 atmospheres and a spacing between anode wires of 2 millimeters, a positive voltage on the order of about 2,500 to about 5,000 volts relative to the cathode wires can be employed.

FIG. 8–12 illustrate how the filter elements and detector cooperate to narrow the energy band of detected radiation in the present invention. For radiographic imaging with the illustrated system, the preferred energy band ranges from about 35 KeV to about 50 KeV. (The graphs illustrate X-ray energies from about 27 KeV to 55 KeV; photons having energies below 27 KeV are typically absorbed by the patient's body and do not reach the detector.)

Figure 8:
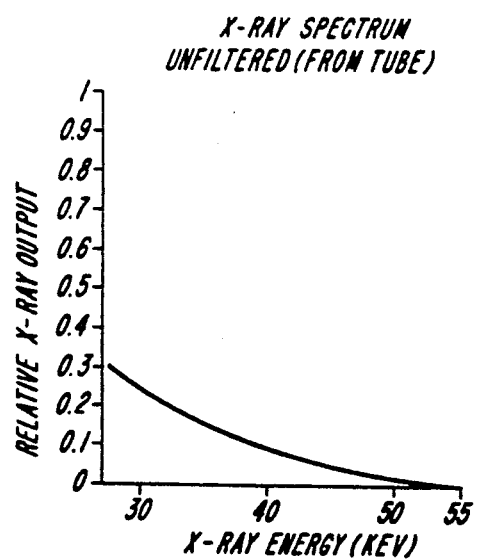
FIG. 8 is a graph showing a typical raw energy spectrum of an X-ray source, such as shown in FIG. 3.

When an X-ray tube or the like is used as a radiation source, photons having a spectrum of energy levels are produced as illustrated in FIG. 8. The upper limit on the spectrum (i.e., 55 KeV in FIG. 8) is obtained by controlling the voltage applied to the X-ray tube. It is preferable to narrow this raw spectrum so as to achieve higher spatial resolution.

In the illustrated multi-wire proportional chamber (MWPC) detection system, Xe gas is used as the radiation detecting element. Photons of energy below 34 Kev can ionize the Xe atoms and produce L-shell electrons, having energies equal to the energy of the photon minus 5.0 Kev (L-edge of Xe); likewise, photons with energy greater than 34.5 Kev can ionize the Xe atoms and produce K-shell electrons, the kinetic energy of which is the difference between the photon energy and 34.5 Kev, the K-edge for Xe.

An electron with a given kinetic energy will be able to travel a finite range in the gas before it collides and ionizes other Xe atoms very close to the anode wire. At pressures below 5 atmospheres, the typical operating range of an MWPC device, the range of the electron can have a very deleterious effect on the spatial resolution of the image obtained by detecting the radiation transmitted though an object (i.e., bone) via the MWPC detector. For example, if a photon interacted at a point in the gas, created a free electron, and the electron traveled to another point where it caused an avalanche at a chamber wire, the initial photon interaction site in the gas could be one or two wire spacings away from it initial interaction site. The result is that information as to where the initial interaction occurred then becomes very imprecise and, hence, lost of spatial resolution in the image of the object occurs.

It is the accurate identification, as close as possible, of the initial interaction site between the photon and Xe atom which results in the spatial resolution of the imaged object. Accordingly, it is preferable to minimize the electron range since this range is always added to the intrinsic spatial resolution of the area detector (MWPC), itself. In practice, the latter can range anywhere from 0.5 to 2.0 mm, depending on chamber design.

It has been discovered that a composite K-edge filter using 2 or more, preferably 3, pure metals stacked on one another, is particularly useful in modifying the raw spectrum of a radiation source to achieve greater spatial resolution in the detector. It has been found that metals with atomic numbers from 45 to 52 (usually two metals) combined with at least one metal whose atomic number ranges from 57 to 65 give an optimum spatial resolution in Xe gas detectors. For example, cadmium (Cd), silver (Ag), and gadolinium (Gd) can be particularly useful in combination. Similarly, cadmium (Cd), tin (Sn) and samarium (Sm) form another useful combination filter.

Figure 9:
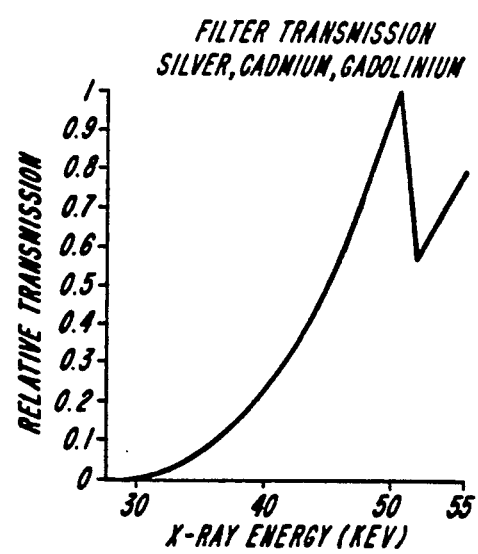
FIG. 9 is a graph showing a typical energy transmission spectrum of a beam filter, such as shown in FIG. 3.
Figure 10:
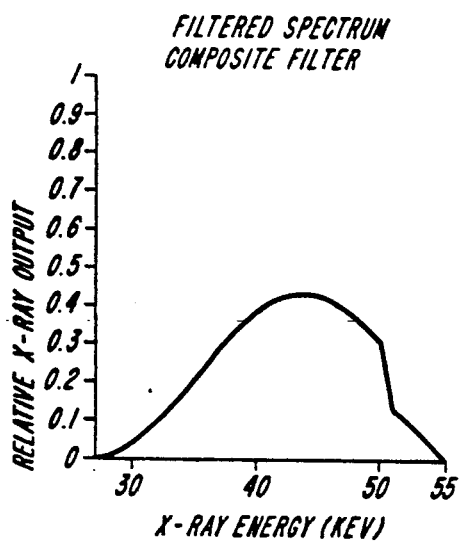
FIG. 10 is a graph showing a typical filtered beam spectrum after passage through a beam filter, such as shown in FIG. 3.

The transmission efficiency of a Cd-Ag-Gd filter combination is illustrated in FIG. 9. As can be seen, the filter combination provides for highest transmissivity in the range of about 42 to about 48 KeV. The results of using this Cd-Ag-Gd filter on the raw spectrum of the X-ray tube is shown in FIG. 10 where a distinctive narrowing of the energy band can be seen. Similar results in terms of limiting the upper range of photons can be achieved for higher X-ray source voltages than 55 Kv by modifying the thickness of the filter elements.

Figure 11:
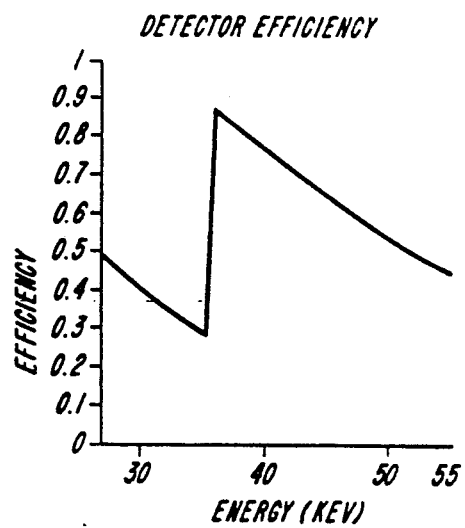
FIG. 11 is a graph showing typical detection efficiencies versus beam energy for a detector, such as shown in FIG. 3.
Figure 12:
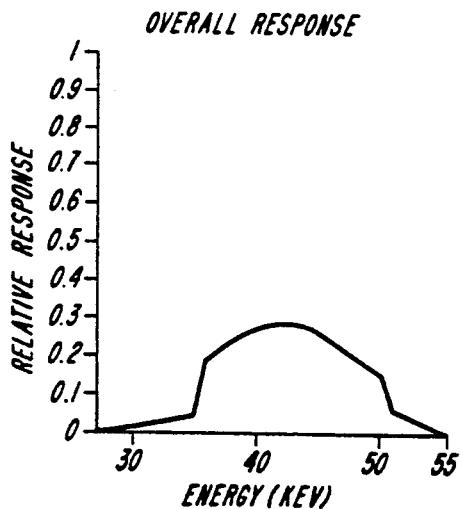
FIG. 12 is a graph showing the overall energy response of a radiographic imaging system according to the invention.

Additionally, the characteristic response of the detector can also be used to further narrow the energy band. In FIG. 11, the efficiency of an MWPC device is plotted, showing that the Xe gas chamber is most effective in detecting photons having energies above 35 KeV and below 50 KeV. When the filtered X-ray spectra is detected in the MWPC device, the overall response, as illustrated in FIG. 12, is a well-defined energy band with sharp edges.

The ultimate result of using the composite filter is twofold: first, by blocking low energy photons, it reduces the radiation dose otherwise absorbed by the patient and, second, by narrowing the energy band of the photons from the source, it dramatically diminished the projected electron range in the detector, itself, thereby improving spatial resolution. The particular advantages of the composite filter can be seen in Table 1 below, where the X-ray tube was controlled so as to impose an upper limit on the photon energy spectrum of 55 KeV and various filter combinations were compared under the same conditions (i.e., same total metal thickness regardless of composition):

TABLE 1

| FILTER EFFECTS ON ELECTRON RANGE IN XENON | | | |
|---|---|---|---|
| | Filter 1 | Filter 2 | Filter 3 |
| No Filter | (Ag) | (Ag + Cd) | (Ag + Cd + Gd) |
| electron range 0.92 mm | 0.56 mm | 0.47 mm | 0.36 mm |

Another result of the composite filter lies in its ability to reduce the error typically inherent in bone mineral content (BMC) measurements due to the presence of fat in the soft tissues of the wrist and forearm. As described in more detail below, to make bone mineral content measurements, one typically measures the intensity of photons through a tissue equivalent bolus which is the same thickness as patient's limb and which contains a material having an absorption characteristic which is the same as tissue free of fat. In actual operations, the fat content can be significant (e.g., five to fifteen percent) in heavy individuals; and when it varies, it will lead to errors in measurement from year to year. Since the composite filter removes a large percentage of the photons in the range 20 to 35 Kev where the difference between the absorption coefficients for fat and tissue is largest, the observed differences in photon intensity through fat-containing tissue will be reduced substantially for the filtered X-ray spectra.

Figure 13:
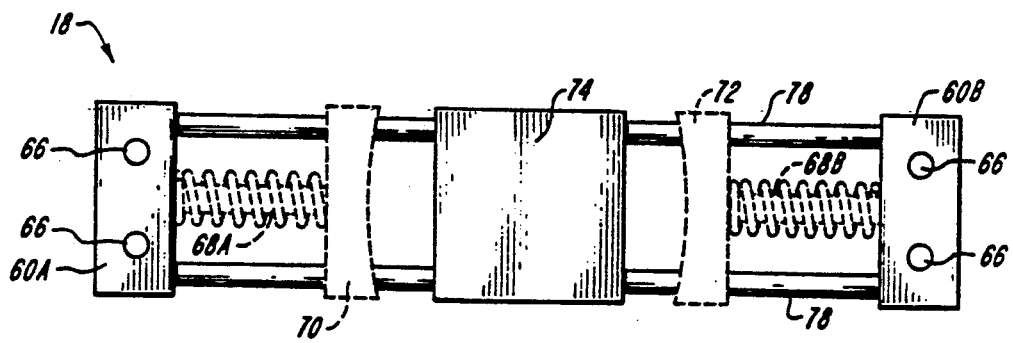
FIG. 13 is a more detailed schematic top view of a limb positioning and calibration device of the system of FIGS. 1 and 2.
Figure 15:
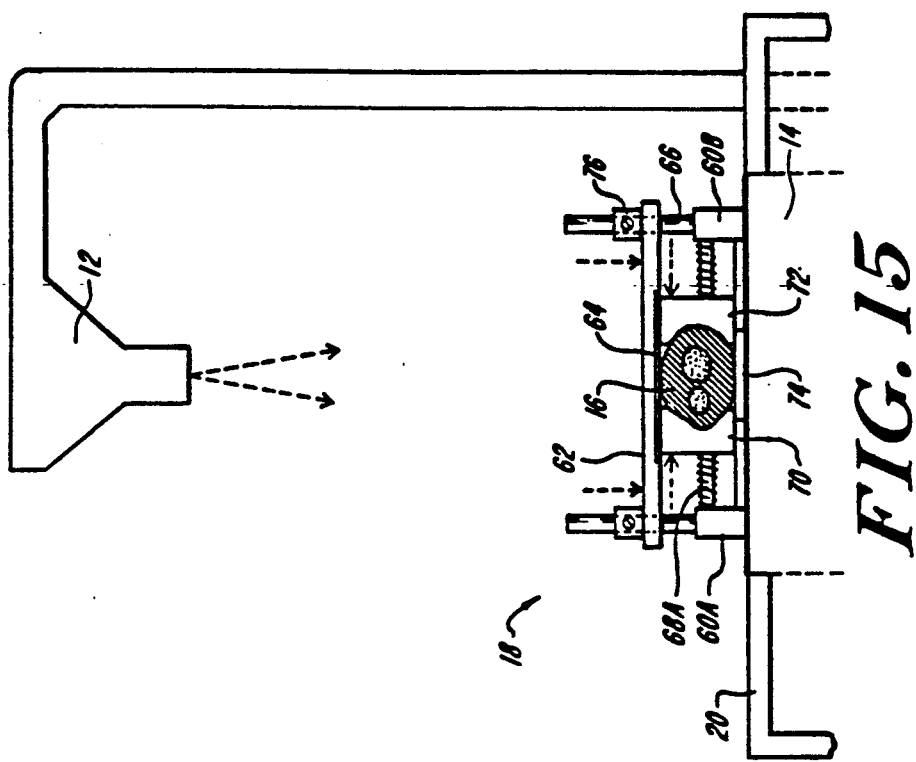
FIG. 15 is a schematic side view of the positioning and calibration device of FIGS. 1 and 2 in a closed position.
Figure 14:
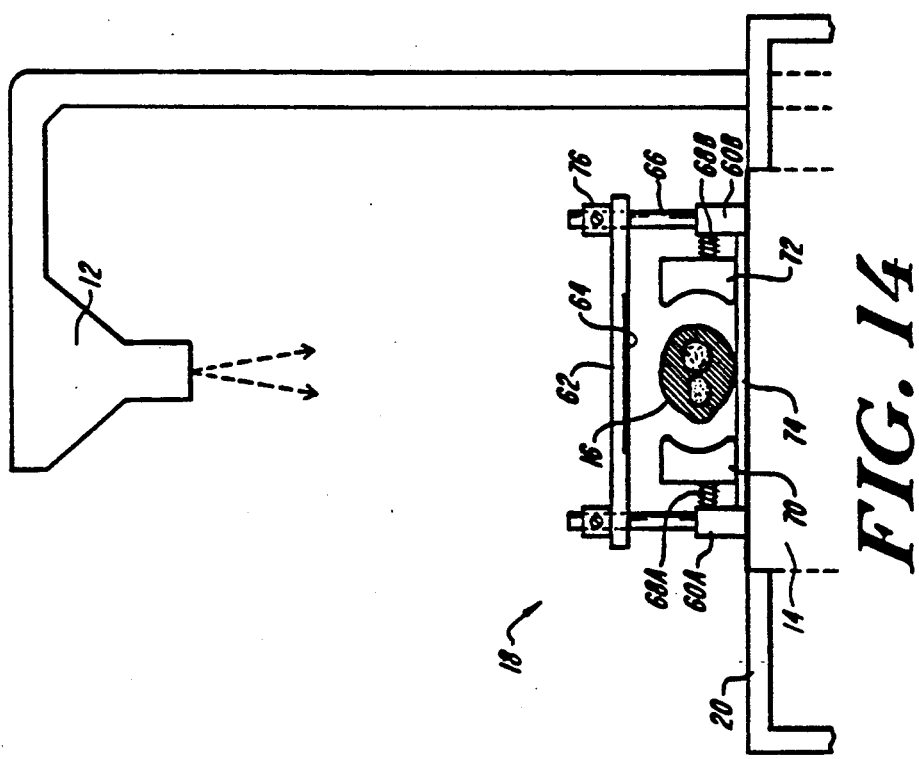
FIG. 14 is a schematic side view of the positioning and calibration device of FIGS. 1 and 2 in a closed position.

FIGS. 13–15 illustrate a limb positioning and calibration apparatus 18 according to the present invention. In FIG. 13, a top view of the apparatus 18 is shown, including end blocks 60A, 60B, a plurality of top posts 66, a plurality of tracks 78, bottom plate 74 (which is composed of a tissue equivalent material), spring-loaded biasing elements 68A, 68B and two side blocks 70, 72, which engage the sides of the patient's limb in operation. In a preferred embodiment, the side blocks are composed of two different materials; for example, side block 70 can be composed of a bone equivalent material and side block 72 can be composed of a tissue equivalent material. Such materials are well known in the state-of-the-art of bone densitometry.

FIGS. 14 and 15 show further features of the limb positioning and calibration apparatus 18 and illustrate its operation. In FIG. 14, the apparatus is shown in its opened position affixed to the housing 20 and disposed below the radiation source 12. As shown, the apparatus further includes a top cover 62 (at least a portion of which is composed of a tissue equivalent material 64) which is attached to the end blocks 60A, 60B via a plurality of post clamps 76. In FIG. 15 the apparatus 18 is shown in its closed position.

In operation the limb 16 is positioned in the apparatus 18 such that side blocks 70 and 72 are pressed by the biasing elements 68A, 68B against the sides of the limb 16 and preferably conform to its shape. For example, the blocks 70, 72 can have a minimum gap, no tension, of about 3 centimeters when in the closed position. In operation, the blocks 70, 72 are separated and the limb (e.g. a wrist) is placed in the gap and then the blocks are allowed to close against the limb due to force of the biasing elements 68A, 68B. To achieve conformation shaping, the blocks can be formed from a flexible plastic shell and filled with fluid, both the plastic and fluid being chosen to provide a calibration equivalence (e.g.

bone equivalence in the case of block 70 and tissue equivalence in the case block 72).

For example, when a wrist measurement is made, the patient's elbow is positioned so that the wrist and forearm are in approximately a straight line. The liquid-filled flexible material contained in blocks 70 and 72 will then form a tight junction and eliminate the gaps near the edge of the wrist that otherwise would occur. The bottom part of the wrist will lie on bottom plate 74, which is also preferably a bed of tissue-equivalent material encased in a plastic covering. Next, a top plate 62 which includes an upper tissue equivalence material is lowered onto the wrist 16. The top and bottom plates 64, 74 of the apparatus 18 are made flush with the top and bottom of the wrist to give the same thickness as the wrist for the side blocks 70, 72. This is accomplished by forcing the top plate 62 down to compress the flexible side blocks on each side of the wrist. The vertical force necessary to compress the side block via the coverplate can be that applied by the operator or the coverplate itself can also be spring-loaded (not shown). A thin layer of flexible filled material 64 may also be incorporated in the bottom surface of the top plate 62 so as to ensure a precise fit. Then the coverplate can be secured by simply turning the screws 76 that lock the coverplate in place via the posts 66.

As noted above, the side blocks 70, 72 preferably incorporate two separate equivalence materials, one for tissue and one for bone, to permit calibration of the system. Such calibration is important to verify results from one machine to another or from session to another, perhaps a year or more later. By use of the two equivalence materials during radiographic imaging, the system can be calibrated to negate possible changes in the energy spectrum of the radiation source or in the detector efficiency.

In one embodiment, calibration can be achieved by taking the natural logarithm of the intensity of radiation transmitted through the two equivalence materials. The ratio of these values can then be used to establish a measurement constant as follows:

$$\ln(I_b/I_t) = U_b/U_t = k \tag{1}$$

where $I_b$ is the intensity of radiation transmitted through a first (e.g., bone equivalence) material, $I_t$ is the intensity of radiation transmitted through a second (e.g., tissue equivalence) material, $U_b$ is the bone absorption coefficient, $U_t$ is the tissue absorption coefficient and k is the measurement constant at which the system desirable operates. (It should be clear that the two calibration materials need not be bone and tissue equivalents: any two materials of differing absorption characteristics can suffice. However, bone and tissue equivalency are preferred to assist in imaging resolution and contrast adjustments, as well).

The calibration apparatus of the present invention thus permits the operator to measure the ratio of $U_b/U_t$ and then dynamically adjust the system prior to patient imaging until a desired measurement constant is achieved. Such adjustments will typically involve varying the intensity of radiation source (e.g. by adjusting the voltage applied to the X-ray tube) or modifying the sensitivity of the detector module. Alternatively, any deviation from the desired measurement constant can instead be noted and used subsequently by the data acquisition or data processing modules to apply a correction factor to the data values. (It should also be apparent that the calibration system of the present invention is useful not only in single energy photo systems but also in so-called "dual photon" systems which detect radiation at two different radiation levels to image bones or conduct bone mineral content analyses.)

The calibration system of the present invention also permits the user to accurately determine the thickness of the limb without resort to physical measurements (e.g., with a caliber). By comparing the logarithmic intensity values of radiation transmitted through the two calibration materials, the thickness of the materials can be calculated. Since the clamping means 18 will constraint the materials to have the same thickness as the limb, the limb thickness can also be inferred. Thus, this thickness T can be calculated according to the following equation:

$$T = \frac{\ln(I_b) - \ln(I_t)}{U_b - U_t} \tag{2}$$

where $\ln(I_b)$ is the natural logarithm of the measurement radiation intensity transmitted through a first calibration material (e.g., a bone equivalence medium) and $\ln(I_t)$ is the natural logarithm of the measurement radiation intensity transmitted through a second calibration material (e.g., a tissue equivalent material and $U_b$ and $U_t$ are the radiation absorption coefficients of the first and second calibration materials, respectively.

Figure 16:
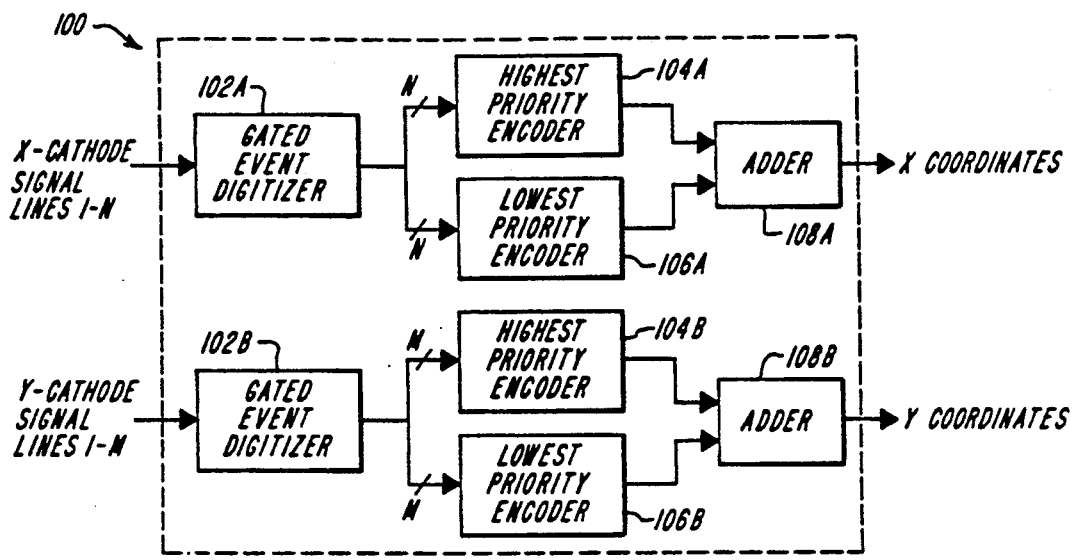
FIG. 16 is a schematic block diagram of the data read-out circuitry of FIG. 6.

FIG. 16 is a more detailed block diagram of the data readout circuitry 100 shown schematically in FIG. 6. The data readout circuit 100 includes gated event digitizers 102A and 102B, highest priority encoders 104A and 104B, lowest priority encoders 106A and 106B and adders 108A and 108B. Each of the X-cathode signal lines are connected to gated event digitizer 102A which produces a synchronized set of digital signals representative of the X-cathode wires which have "sensed" a radiation event. The highest priority encoder 104A selects the highest X-cathode wire for which a positive digital signal has been generated and produces a digital number corresponding to the highest wire. Likewise, the lowest priority encoder 106A selects the lowest X-cathode wire for which a positive digital signal has been generated and produces a similar digital number corresponding to the lowest wire. By summing the outputs of encoders 104A and 106A, and dividing by two, the origin of the radiation event on the X-coordinate axis can be determined.

A similar operation is performed by digitizer 102B, encoders 104B and 106B, and adder 108B to arrive at the origin of the radiation event on the Y-coordinate axis. (In practice, one does not need to divide the outputs of adders 108A and 108B by two, since the sum values will define a new spatial matrix twice the size of the original grid, and thereby, permit recordal of events with greater spatial resolution. The practical result is a resolution equal to one-half of the line spacing.)

Figure 17:
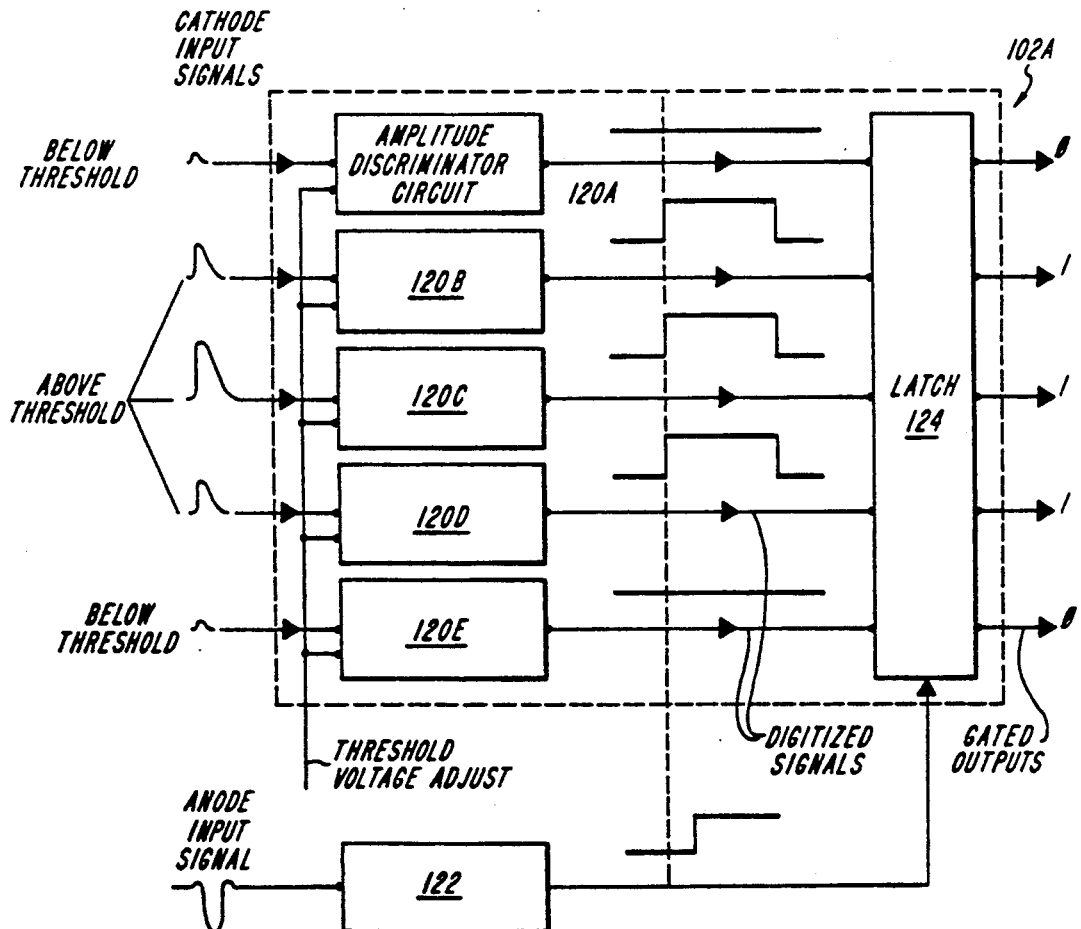
FIG. 17 is a more detailed diagram of a gated event digitizer as shown in FIG. 16.

In FIG. 17, the components of one of the gated event digitizers 102A are illustrated in more detail. As shown, digitizer 102A includes a plurality of amplitude discriminator circuits 120A-120E. (Although five discriminator circuits are shown for purposes of illustration, the total number of discriminators in practice will equal the total number of X-cathode lines.) The lines which feed the discriminator circuits will be impressed with analog electrical signals of varying amplitudes depending upon their distance from the radiation event. The discriminator circuits are set by an adjustable threshold voltage to produce a digital output signal when the associated cathode line "senses", an electrical signal above the threshold. The digital outputs of the discriminator circuits 120A-E are registered by latch 124, which in turn, is triggered by a digital enablement signal generated by a similar discriminator circuit 122 connected to the anode grid. (Although a single anode input signal is shown, it should be clear that other embodiments can include a plurality of anode sensors to detect a negative signal anywhere on the anode grid.) The coincidence of the anode and cathode signals above their respective thresholds yields a set of gated outputs to the encoders 104A and 106A of FIG. 16, thereby permitting a determination of the X-axis location. An identical circuit, with a different number of input and output lines when the detector area is not square, is employed in gated event digitizer 102B of FIG. 16 to obtain the Y-cathode signals and, ultimately the Y-coordinate location of the radiation event.

Figure 18:
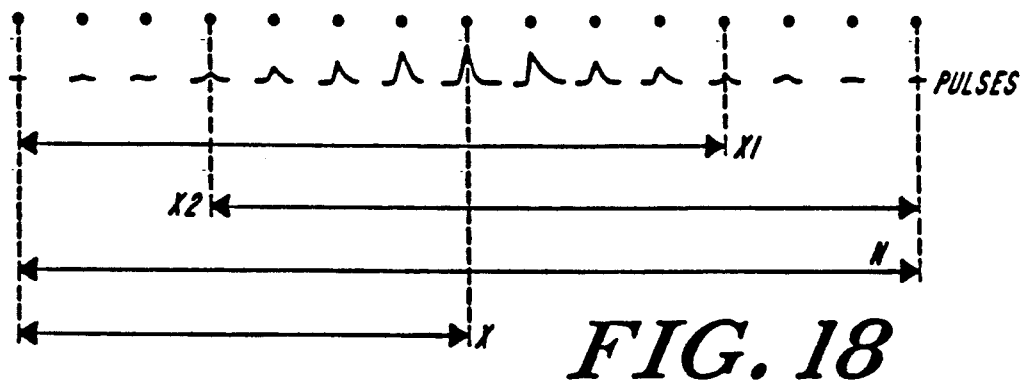
FIG. 18 is a graphic illustration of the priority encoding operation performed by the circuitry of FIG. 16 to obtain an event coordinate.

The "center of cluster" principle for determining radiation event locations in the priority encoders is shown in more detail in FIG. 18. Pulses of varying amplitudes are sensed by the N x-cathode lines. To determine the center of the signal cluster (X) and, hence, the origin on the X-axis of the radiation event, the priority encoders first determine (X1) and (X2), the locations of the end points of the pulse distribution. The center (X) can be calculated as follows:

$$X = (N - X2) + \frac{X1 - (N - X2)}{2} = \frac{N + X1 - X2}{2} \quad (3)$$

Again, an analogous calculation is made for the M Y-cathode lines to determine the center of the Y-cathode signals.

Figure 19:
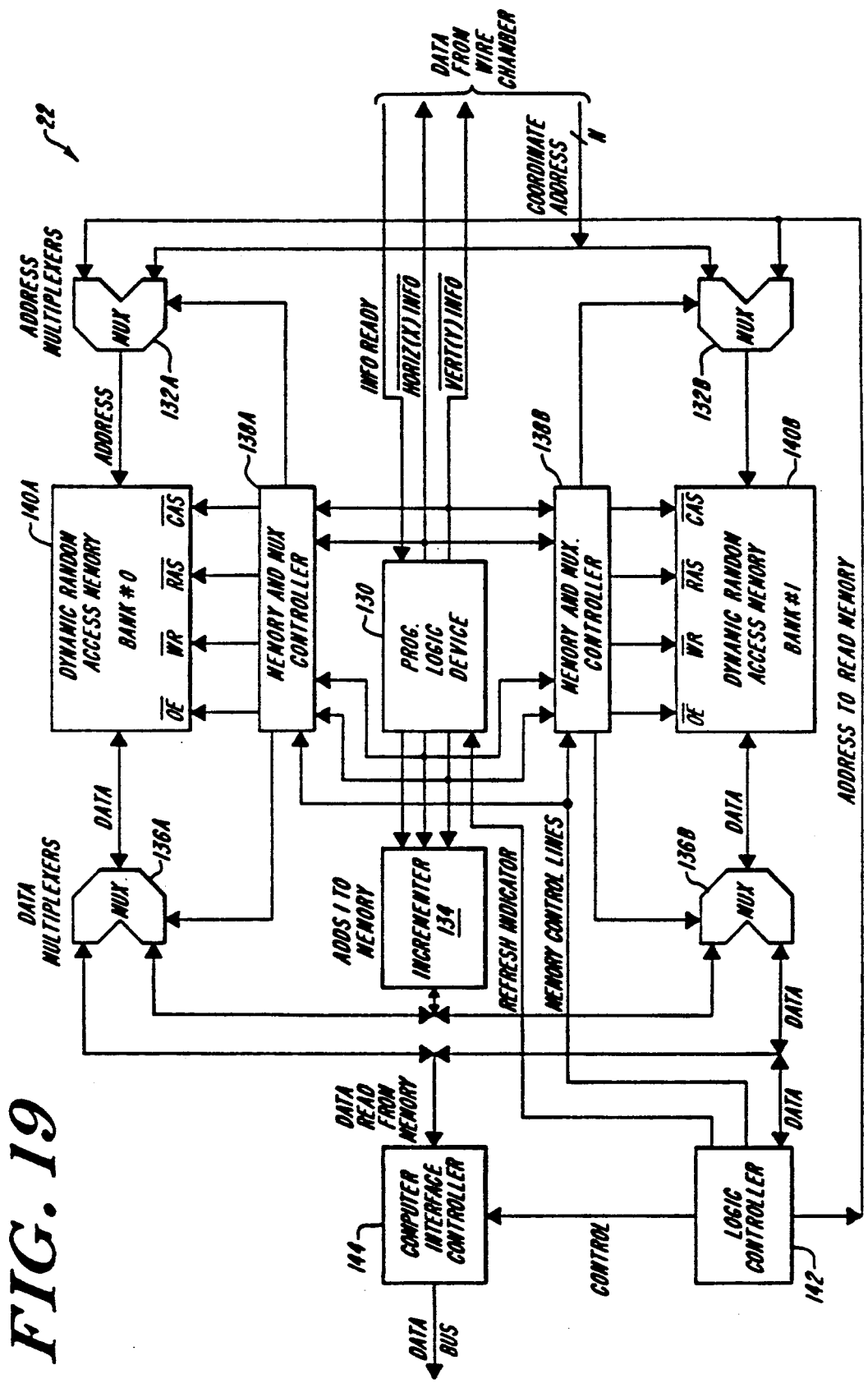
FIG. 19 is a schematic block diagram of data acquisition circuitry useful in the system of FIG. 2.

FIG. 19 is a more detailed block diagram of the data acquisition module 22 shown schematically in FIG. 2. The data acquisition module 22 includes programmable logic device 130, address multiplexers 132A, 132B, incrementer 134, data multiplexers 136A, 136B, memory and multiplexer controllers 138A, 138B, dynamic random access memory banks 140A, 140B, logic controller 142 and a computer interface controller 144.

As shown in FIG. 19, the data acquisition module is formed from two separate memory subassemblies, each consisting, for example, of a standard $512 \times 512 \times 16$ bit memory operated by a common programmed logic device 130 and logic controller 142. When a given memory is filled, the logic controller 142 directs new events to the other memory bank and proceeds to transfer the contents of the first memory bank through the computer interface controller 144 to a data processing module, a data display module or a data storage module.

The memory banks 140A, 140B each can each be constructed as a single $512 \times 512$ pixel image memory, or they can be partitioned to represent multiple smaller images, such as for example, four $256 \times 256$ pixel images or sixteen $128 \times 128$ images. Any of these arrangements permits the system to take multiple frames of data sequentially in time; each memory bank (or partition) thus acts as a histogram creating an image based upon radiation events recorded over time. Since the module 22 permits one memory bank to be transferred as the other is filled, it is possible to process or store data continuously.

The computer interface controller 144 is preferably a small computer systems interface (SCSI) which is compatible with a wide variety of computer hardware, thereby allowing data transfer continuously, in either frame or list mode, to an external computer memory and/or an external magnetic or optical memory hard disk. Moreover, since the SCSI standard supports multiple SCSI devices on a single bus, it is possible to have several data acquisition systems operating in parallel from the same or multiple sources.

The logic controller 142, incrementer 134 and programmed logic device 130 of FIG. 19 cooperate to acquire and transfer data from the detector module, which can be a multiwire proportional chamber device, as described above, or another type of imaging device, such as a gamma camera or other photon imager. The logic controller 142 can be constructed from a general purpose microprocessor, such as the HD64180 microprocessor manufactured by Hitachi (San Jose, Calif.) and/or other commercially available parts. The microprocessor is preferably configured to define a direct memory data access channel for fast transfer of data between the memory banks 140A, 140B and the computer interface controller 144, and serves to refresh the dynamic random access memories periodically as well as initialize the programmed logic device 130, and multiplexers 132 and 136 and activate the interface controller 144.

The microprocessor is programmed to perform tasks in response to requests by either the computer interface controller or other events that signal the end of a data acquisition cycle. In a typical sequence, the computer interface controller 144 will alert the logic controller 142 of a pending host computer request. This request can be, for example, an order to commence acquiring data from a wire chamber detector. The logic controller 142 will then decide which of the memory banks is to be used for this data acquisition cycle and set up the memory controllers 138 for that purpose. The logic controller 142 will also signal the programmed logic device 130 to begin acquiring data as described below. In addition, the logic controller 142 can initiate an internal timer to stop the data acquisition process after a predefined time has elapsed. Alternatively, it can program an event counter to stop data acquisition after a predefined number of events have been recorded.

A host computer may also request from the logic controller 142 the initiation of data transfer from a previously acquired frame. The logic controller 142 will then direct the memory controllers 138 and multiplexers 136 and 132 to connect the corresponding memory bank 132A or 132B to the data path of the computer interface controller 144. The logic controller 142 will then set up the parameters of a direct memory access controller to sequentially read the locations of the memory bank and simultaneously write them to the computer interface controller 144.

The incrementer 134 can be implemented by a parallel load counter, such as the model 74F779 counter manufactured by National Semiconductor, Fairchild Division (Mountainview, Calif.). The programmed logic device 130 can also be implemented with a commercially available, programmable logic device such as the model 20R4 device manufactured by Advanced Micro Devices (Sunnyvale, Calif.).

The various multiplexers and memory elements also shown in FIG. 19 are conventional in design and can be implemented with a wide variety of commercially available components. It should be clear that various changes, additions and subtractions to the circuitry of FIG. 19 can be made by those skilled in the art without departing from the spirit or scope of the invention. For example, the memory and mutiplexer control functions of elements 138A, 138B can be supported by separate bit slice processor elements or can be implemented by firmware as part of the logic controller 142 or the programmed logic device 130. Obviously, the functions of the components illustrated in FIG. 19 can be combined into larger integrated circuits or divided into smaller processing elements.

In one preferred embodiment, the programmed logic device 130 is implemented as a state machine with eight states. The device 130 permits very fast acquisition of histogramming information by addressing a location in one of the memory banks, which corresponds to the particular coordinate location in the detector module where the radiation event occurred, retrieving the contents of the memory location and presenting it to the incrementer 134 which adds a "1" to those contents, and then rewrites the new number to the addressed memory location.

Figure 20A:
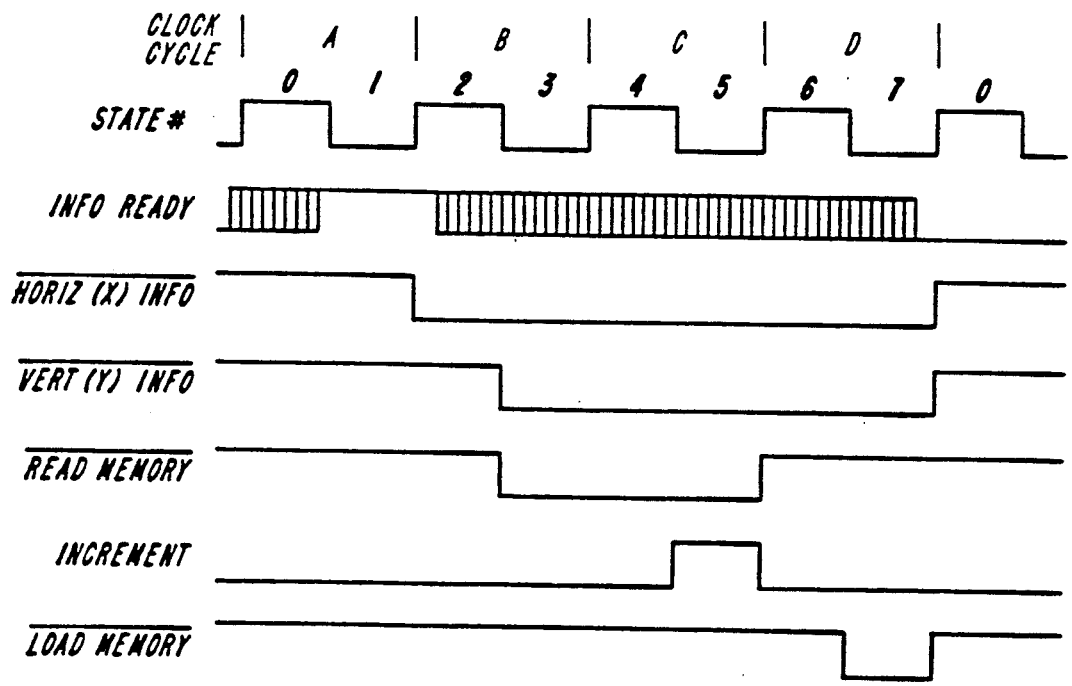
FIG. 20A is a timing diagram for a programmable logic device as shown in FIG. 19 and is further illustrated schematically in FIG. 20B and by a state diagram FIG. 20C.
Figure 20B:
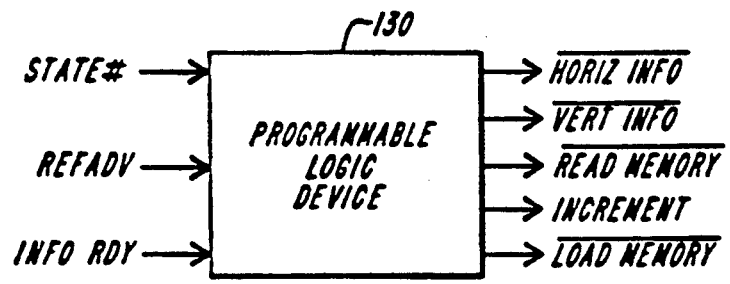
Figure 20C:
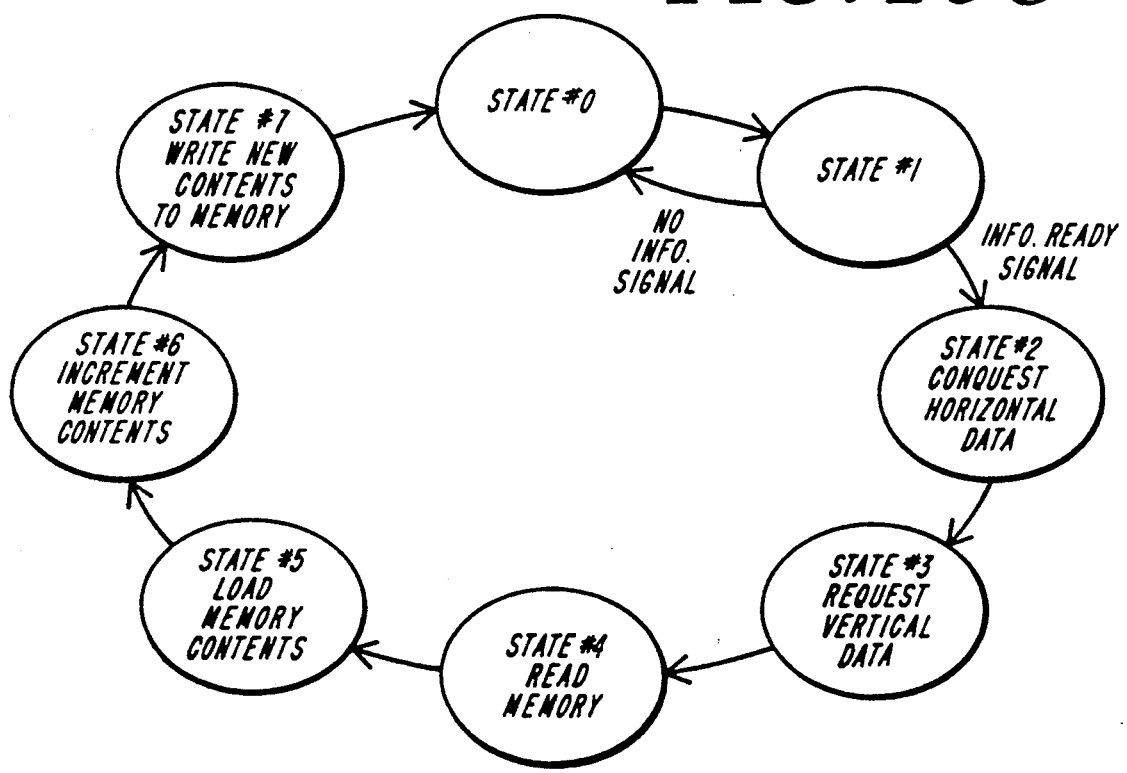

The functions of programmed logic device 130 can be further understood by reference to the timing diagrams of FIG. 20A which shows four clock cycles (denoted as A, B, C and D) and further by the schematic diagram of FIG. 20B and the state diagram of FIG. 20C. As shown, the state machine has the following sequence:

In the idle mode, the state machine cycles between state #0 and state #1 during each clock cycle. If the detector module signals a new event by asserting the INFO READY line during the first half of clock cycle A (i.e., state #0), the state machine switches to the active mode.

The second half of the clock cycle A provides a timing safeguard to insure that the INFO READY signal has been received.

Next, during the first half of clock cycle B (i.e., in state #2), the horizontal (or x) information is requested from the detector module, which is latched as row information in the DRAM-based memory bank 140.

During the second half of clock cycle B (i.e., state #3), the vertical (or y) information is requested from the detector module, which is latched as column information in the memory bank 140. At this point, the present contents at the location X-Y in the memory bank 140 are retrieved. The output buffers are enabled, and the incrementer is ordered to load the contents (READ MEMORY signal).

In the following clock cycle C, the first half of this cycle (i.e., state #4) provides a timing delay to ensure that the memory contents have been loaded into the incrementer.

By the second half of clock cycle C (i.e., state #5), the present contents of the X-Y position have been loaded in the incrementer 134, and an order to INCREMENT has been given.

The first half of the final clock cycle D (i.e., state #6) again provides a timing delay to insure that the incrementer has completed it task.

The second half of clock cycle D (i.e., state #7), an order is given to the incrementer 134 to output the new data, while simultaneously writing said data to the position X-Y in the memory bank 140 (MEMORY LOAD signal).

The operation of logic device 130, as detailed above, can be further understood by reference to the state diagram of FIG. 20C.

The programmed logic device can be driven at any clock rate compatible with the other components of the system. For example, when a 10 MegaHz clock is employed, the state machine cycle through its eight states as shown in FIG. 20A in four clock cycles, or approximately 50 nanoseconds per state. A faster clock can also be employed to further reduce the data acquisition time.

The input signal labeled REFADV indicates to the state machine that a DRAM-refresh cycle is about to take place. The state machine refrains from initiating the 8 state sequence while this signal is asserted.

The DATA READY signal, used by the wire chamber system to indicate availability of data, may be withdrawn by state #3, and must be withdrawn by state #7.

While reading the histogramming memory 140, the general purpose logic controller 142, and not the programmed logic device 130, preferably, generates the necessary control signals to retrieve the information from the memory 140 and presents it to the computer interface controller 144. When data transfer from a memory element to the computer interface controller 144 is taking place, no data acquisition can be performed to that histogram memory and vice versa.

With reference again to FIG. 19, the data acquisition module 22 provides for simultaneous buildup of a histgram, and transfer of data to the computer interface controller 144 of a previously-acquired histogram, by employing two identical histogramming memory banks 140A, 140B. This prevents loss of data acquisition information while reading previously acquired information.

A plurality of two-position multiplexers or digital switches are incorporated for this purpose. They provide a connection of each of the histogramming memory banks 140A, 140B to the data acquisition or data transfer address and data lines. Two unidirectional multiplexers 132A, 132B—labeled ADDRESS MUX—route either the wire chamber information or the logic controller generated address to the corresponding memory banks. Two bidirectional multiplexers 136A, 136B—labeled DATA MUX—route the histogram information to the incrementer 134 (when in a data acquisition cycle) or to the computer interface controller 144 (when in na data transfer cycle).

The multiplexers, for one of the histogramming memory banks, are always in the opposite position, as the ones for the remaining histogram memory. The one exception is during the DRAM refresh cycle (generated by the logic controller 142), in which both address multiplexers 132A, 132B are connected to the logic controller 142.

Figure 21:
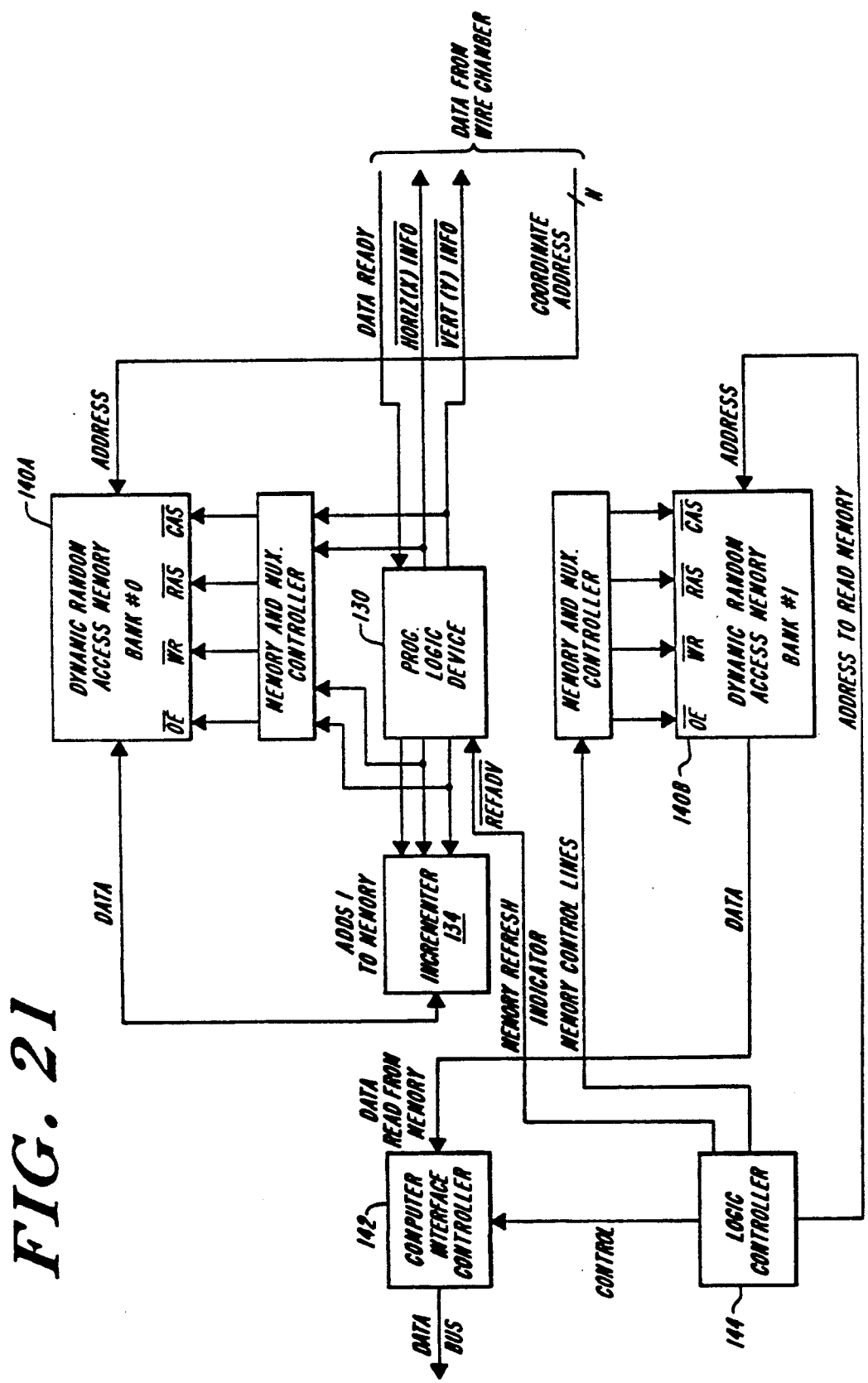
FIG. 21 is a schematic illustration of a data flow path within the circuitry of FIG. 19.

FIG. 21 illustrates the data flow path during a typical portion of the acquisition cycle. In this figure, the acquisition module 22 is shown in a state where memory bank 140A is acquiring data, while memory bank 140B is transferring data through the computer interface controller 144.

Returning to FIG. 2, the remaining elements of system 10, the data processing module 24, a data display module 26 and a data storage module 28 can all be assembled from commercially available components. For example, a wide variety of general purpose microcomputers, minicomputers or mainframe computers can be employed to process the data in the data processing module 24. Similarly, a wide variety of computer monitors or higher resolution video display equipment can be employed in the display module 26. In accordance with conventional image generation techniques, the image presented to the operator can be composed of pixels having gray-tone levels or color values which are representative of the detector responses at given areas of the patient's limb being imaged. The data storage module 28 can also be of conventional design and rely on any one of a number of known storage media, such as magnetic disks, diskettes, tape cassettes, optical disks, or solid-state random access memory elements.

In one preferred embodiment, the data processing module 24 and the display module 26 can be used cooperatively to perform measurements of bone density on a particular bone structure or bone structures of the patient's limb being imaged. A procedure for such imaging and bone density measurements, which can be implemented by software, firmware, or a combination thereof, in the data processing module 24, follows with reference to FIGS. 22-24, which are illustrative of the bone structures of a patient's wrist.

In FIG. 22, an overall schematic view of the presentation of a patient's limb 16, in this instance, a wrist, to the system is shown. The bone structure of the patient's limb 16 in shown in phantom, except for that portion 150 which is actually viewed by the detector. As can be seen from this schematic illustration, the two principal bone structures in the wrist image are the radius 152 and the ulna 154. The data processing module of the present invention employs the styloid tips of the radius and the ulna bones as reference points, and establishes measurement areas in select regions of those bones that contain high percentages of trabecular bone, rather than cortical bone. These select regions, in the case of the radius and the ulna, have been determined to lie at specific distances from the respective styloid tips of these bones.

In practice, to improve sensitivity in detecting bone loss, it is important to measure areas that contain high percentages of trabecular bone. Thus, in accordance with the invention, measurement areas are selected that contain 60% or more of trabecular bone. The percentage of trabecular bone present in the radius and the ulna beyond 30 millimeters from the styloid tip of each bone drops below 10% and the percentage of cortical bone for both the radius and the ulna is approximately 95% at points beyond 40 millimeters from the styloid tip.

It has also been determined that the region associated with this 60% limit of trabecular bone usually begins at 2 millimeters and 4 millimeters, respectively, from the styloid tips of the radius and the ulna, respectively. The highest trabecular content by volume is typically found about 9 millimeters to 20 millimeters from the styloid tip in the radius and between about 4 millimeters and 12 millimeters from the styloid tip in the ulna. In accordance with the invention, therefore, bone mineral content measurement regions are selected within each of these areas of high trabecular bone content.

In use, the operator can perform a bone mineral content measurement by employing the data processing module 24 and data display module 26 together. In one typical protocol, the system is initialized and an image is displayed to the clinician via a conventional computer monitor. The resolution of the display is not critical, so long as the bone edges are identifiable by the operator. In one preferred embodiment, the operator is prompted to use a cursor control device, such as a conventional mouse or joy stick, to place the styloid tip region markers around the respective styloid tips of the radius and the ulna. These markers may include, for example, hollow rectangular region markers, similar to styloid tip markers 166 and 168 shown in FIG. 23, which depicts a more detailed radiological image of a human wrist. In the illustrated embodiment, the data processing module executing the method steps of this invention reads the position of the styloid tip region markers to generate initializing data for the location of the styloid tips.

The location of edges surrounding the styloid tips within each marker region can be determined by techniques known in the art. Bone edge finding can be implemented in accordance with any conventional edge finding algorithms, such as those disclosed in J. F. Canny, *Tech. Rep.* 720, Artificial Intelligence Laboratory, MIT (1983); "A Computational Approach To Edge Detection," Vol. PAMI-8 *IEEE Trans. Pattern Anal. Machine Intell.* (1986) or F. Bergholm, "Edge Focusing," Vol. PAMI-9 *IEEE Trans. Pattern Anal. Machine Intell.* (1987). Preferred edge finding algorithms include those which reduce noise contributions in the images and optimize the location of single edges rather than multiple spurious edges.

The edge finding step is followed by a positional search executed on the edges of the styloid tip to identify one or more pixels that define the extremity of the styloid tip on each bone. Because the precise point-by-point shape of the respective radial and ulnal styloid tips can differ from individual to individual, it can be useful to employ more than one form of positional search or a curve fitting routine to determine the extremity of each styloid tip. The search or curved fitting routine can include a technique which finds the minimum-gradient tangent between points defining the edge, or one which locates the intersection of curves fitted to the styloid tip edges.

As an alternative to reading and responding to operator input and finding the styloid tips, the invention can utilize known techniques for initializing edge finding on the outer edge of the radius or ulna and progressing up and around the styloid tips to determine the edges of the bone extremities. However, utilization of operator input reduces processing time. Moreover, the step of responding to operator input increases accuracy over a fully automated system, because it is likely that bone edges other than those of the radius and ulna will be present within the styloid tip region of interest. The phenomenon is illustrated in FIG. 23, where the edges of the scaphoid bone 156 near the radius, and the lunate bone 158 near the ulna, are proximate to the styloid tips 162 and 170. When the styloid tip locations have been determined, one or more pixels identifying the extremity of the tip can be highlighted on the display for inspection by the operator, to confirm proper identification of the styloid tips.

Next, the data processing module executes a further edge finding step to determine the inner and outer longitudinal edges of the radius and the ulna. (As used herein, the term "longitudinal direction" is meant to define the direction corresponding to the long axis of the bone. For purposes of illustration, this longitudinal axis corresponds to the Y-coordinate axis of the detector.)

The initial starting position can be, for example, 3 centimeters from the styloid tip extremity of the radius. This initial position is preferable to ensure that the edge finding occurs in a region having an interosseous gap between the radius and the ulna. Typically, at this position with the wrist in a neutral position (i.e., with no twisting of the wrist off the X-reference plane) the interosseous separation between the ulna and the radius can range from 0.5-2.5 centimeters, depending upon the size and shape of the bones. Thus, by initiating the edge finding process at a selected displacement, for example, approximately 3 centimeters, from the extremity of the styloid tip of the radius, ensures that the edge finding will occur in a region having a gap between the radius and the ulna.

Longitudinal edge finding thus progresses along the bone from the initial position for a selected distance in the direction of a styloid tip and from the initial position for a selected distance in the opposite direction, to identify the edges of the bones on either side of the initial starting position the selected distance can be, for example, 2 centimeters or less from this initial position.

When the longitudinal edge finding process is complete, the widths of each bone can be computed at selected Y-axis positions. A horizontal line, referred to as the "region base line," is then established and displayed at a Y-axis position on each bone having a selected displacement from the extremity of the respective styloid tip. A bone mineral content measurement can then be made on each bone. The measurement regions can be highlighted on display for the inspection of the operator.

As illustrated in FIG. 24 the measurement regions 170 and 172 can be, for example, rectangular in form having a selected height and a selected width based on the bone widths calculated previously. In particular, the measurement regions can extend from bone edge to bone edge, as does measurement region 172 on the ulna 154 in FIG. 24 or, the measurement regions can be reduced by a selected amount, to eliminate the outer and inner edges of the imaged bone from the BMC measurement region. Area 170 on the radius 152 in FIG. 24 is an example of a narrowed measurement region.

In many cases, narrowing the measurement region provides increased sensitivity in BMC measurements by reducing inaccuracies in measurement and computation which can result from highly irregular bone shapes.

The BMC values can be derived in a known manner, by summing pixel intensity values in each measurement region. Bone density values can also be obtained by dividing the BMC value by the size of the measurement regions. The area covered by the measurement regions is proportional to the number of pixels in the measurement region. Those skilled in the art will appreciate that BMC values are proportional to the sum of the values of the data points in the measurement region, which in turn are represented by the pixel intensity values in the measurement region. In particular, the digital number associated with each pixel is typically proportional to the magnitude of the radiation received by the detector in the region corresponding to that pixel.

Processing can be terminated when the BMC and density values have been obtained. Alternatively, the process can be re-initiated for processing of additional radiographic images.

Additional techniques for imaging bone structure and for deriving bone mass in density can be found in commonly owned U.S. patent application Ser. No. 321,764 entitled "Methods And Apparatus For Bone Measurement" filed on even date herewith and incorporated herein by reference.

The present invention also permits a number of additional analyses to be performed from the stored data. For example, in successive bone mineral measurements of the same patient, the currently generated image data can be compared with previously stored images. A comparison can be made between the current orientation of the radius and ulna and the orientation of the radius and ulna represented in the stored data.

In a further preferred embodiment of the invention, a correction factor is established for the X and Y coordinate factors, to correlate previously generated and currently generated images and to correct small errors in the positioning of the patient's limb. Two-dimensional images, such as the bone joint images processed in accordance with the present invention, have defined orientations within an X-Y orthogonal coordinate axis system. Differences in the orientation of the ulna and the radius in successive images can be detected with reference to this X-Y coordinate system.

One technique is to evaluate the gradient at various points along the outer edges of each bone, to identify the flattest portion of the outer edge of each bone. Curve-fitted portions of the currently generated and previously generated bone joint images can than be compared to determine whether small translations and/or rotations of the imaged bones have occurred from one measurement to the next.

While translational transformations in the direction of the Y-axis do not significantly affect the repeatable selection of measurement regions in successive images, rotational transformation should be corrected from image to image. Corrections for rotational transformations can be made by computing the angles between the flat portion of the outer bone edges for each of the first and second images. Based on the computed angles, corrections for both the X-and Y-axis positional pixel values can be provided by known computational techniques. Evaluation of these angles, and the positional values of the extremities of the styloid tips, permits images to be superimposed, or otherwise placed into point-to-point registration, to ensure that the vertical and horizontal bone distances are consistent from image to image for a given individual.

It will be understood that changes may be made in the above construction and in the foregoing sequences of operations without departing from the spirit or scope of the invention. It is accordingly intended that all matter contained in the above description or shown in the accompanying drawings be interpreted as illustrative rather than in a limiting sense.

Having described the invention, what is claimed as new and secured by Letters Patent is:

1. A continuous data acquisition system for radiographic imaging, without interrupting acquisition activity the acquisition system comprising:

at least two memory means for storing radiographic data from a radiation detector wherein each of the memory means having a plurality of addressable memory locations and each of the memory means are such that said locations of the memory means correspond to spatial locations in the radiation detector;

logic control means for sensing radiographic data transmitted by the radiation detector, for selecting one of said memory means for storage of said data, for transferring data to the selected memory means, and for switching from one memory means to another memory means according to a predefined schedule and according to memory capacity level, said logic control means further comprising a logic device which receives data and increments the contents of locations in a memory means in response to such data; and interface control means for reading data from one or the other memory means when such memory means is not actively acquiring data such that data can be acquired continuously by the system.

2. The system of claim 1 wherein the memory locations of said memory means are further arranged to cumulatively store data as histograms in order to generate radiographic intensity images.

3. The system of claim 2 wherein each of the memory means further comprises an incrementer means for incrementing the contents of individual locations of the memory means in response to individual radiation events detected by a radiation detector.

4. The system of claim 1 wherein the logic device further includes means for monitoring a radiation detector to determine when data is available for acquisition.

5. The system of claim 4 wherein the logic device further comprises means for addressing a location in a memory means which corresponds to a particular location in said detector where a radiation event occurred.

6. The system of claim 1 wherein each memory means further comprises a dynamic random access memory device.

7. The system of claim 1 wherein the logic control means further comprises means for determining when one of said memory means has reached a predetermined capacity level, and for switching from one memory means to another when said level has been reached.

8. The system of claim 1 wherein the memory means further comprises means for storing calibration data in conjunction with said radiographic data.

* * * * *